(12) United States Patent
Albert et al.

(10) Patent No.: US 6,458,103 B1
(45) Date of Patent: Oct. 1, 2002

(54) AXIALLY ACTIVATED HEMOSTASIS VALVE WITH LUMEN SIZE SELECTION

(75) Inventors: Kathryn M. Albert, Saratoga Springs; Ronald L. West, Fort Anne, both of NY (US); Theodore C. Lamson, Pleasanton, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/425,466

(22) Filed: Oct. 22, 1999

Related U.S. Application Data (60) Provisional application No. 60/105,384, filed on Oct. 23, 1998.

(51) Int. Cl.⁷ .............................................. A61M 5/178
(52) U.S. Cl. ........................... 604/167.03; 604/167.01; 604/165.02; 604/246
(58) Field of Search ........................ 604/523, 246–250, 604/264, 164.01, 165.01, 165.02, 167.01–167.03

(56) References Cited

U.S. PATENT DOCUMENTS

| | | | |
|---|---|---|---|
| 3,915,167 A | 10/1975 | Waterman | |
| 3,960,149 A | 6/1976 | Bujan | |
| 4,015,336 A | * 4/1977 | Johnson | 251/347 |
| 4,149,535 A | 4/1979 | Volder | |
| 4,187,848 A | 2/1980 | Taylor | |
| 4,345,596 A | 8/1982 | Young et al. | |
| 4,838,269 A | 6/1989 | Robinson et al. | |
| 4,838,873 A | 6/1989 | Landskron et al. | |
| 4,929,243 A | 5/1990 | Koch et al. | |
| D313,849 S | 1/1991 | Robinson | |
| 5,053,015 A | 10/1991 | Gross | |
| 5,125,915 A | 6/1992 | Berry et al. | |
| 5,185,004 A | 2/1993 | Lashinski | |
| 5,195,980 A | 3/1993 | Catlin | |
| 5,338,313 A | * 8/1994 | Mollenauer et al. | 604/249 |
| 5,352,215 A | 10/1994 | Thome et al. | |
| 5,395,352 A | 3/1995 | Penny | |
| 5,458,640 A | 10/1995 | Gerrone | |
| 5,460,615 A | 10/1995 | Storz | 137/849 |
| 5,514,109 A | * 5/1996 | Mollenauer et al. | 604/249 |
| 5,542,933 A | 8/1996 | Marks | 604/167.03 |
| 5,584,808 A | 12/1996 | Healy | |
| 5,599,305 A | 2/1997 | Hermann et al. | |
| 5,693,025 A | 12/1997 | Stevens | 604/167 |
| 5,873,865 A | * 2/1999 | Horzewski et al. | 604/523 |
| 5,921,968 A | 7/1999 | Lampropoulos | 604/246 |

FOREIGN PATENT DOCUMENTS

| WO | WO 98/53874 | 12/1998 |
|---|---|---|

\* cited by examiner

*Primary Examiner*—Brian L. Casler
*Assistant Examiner*—Jeremy Thissell
(74) *Attorney, Agent, or Firm*—Steven A. McAuley (57) ABSTRACT

A hemostasis valve which has a varying diameter. The hemostasis valve is actuated by a mechanism which provides mechanical advantage. Actuation of the hemostatis valve provides selective incremental sizing such that the valve will fit a variety of different intravascular devices.

16 Claims, 10 Drawing Sheets

AXIALLY ACTIVATED HEMOSTASIS VALVE WITH LUMEN SIZE SELECTION

This application claims priority to U.S. Provisional Patent Application Ser. No. 60/105,384, filed Oct. 23, 1998.

FIELD OF THE INVENTION

The present invention generally relates to the field of minimally invasive medicine. More particularly, the present invention relates to those devices, commonly known as y-adapters, which are used to prevent blood from exiting a patient during a minimally invasive procedure. Such procedures include but are not limited to angioplasty, atherectomy, stenting, angiography, venous filtration, liquid infusion, dialysis, and intravascular ultrasound. Those skilled in the art will recognize the benefits of applying the present invention to similar fields not discussed herein.

BACKGROUND OF THE INVENTION

Angioplasty has gained wide acceptance in recent years as an efficient and effective method for treating various types of vascular diseases. In particular, angioplasty is widely used for opening stenoses in the coronary arteries, although it is also used for treatment of stenoses in other parts of the vascular system. The most widely used form of angioplasty makes use of a guide catheter positioned within the vascular system of a patient. The distal end of the guide catheter is inserted into an introducer sheath which is then inserted into the femoral artery located in the groin of the patient and pushed distally up through the vascular system until the distal end of the guide catheter is located in the ostium of the coronary artery. The distal end of the guide catheter is normally curved so that the distal tip of the guide catheter is more easily directed to the coronary ostium of the patient. Typically, a Y-adapter assembly is releasably secured to the proximal end of the guide catheter. The proximal end of the guide catheter and the Y-adapter protrude outside the patient's body. The Y-adapter provides an entryway for subsequent insertion of additional angioplasty devices into the patient's vascular system through the guide catheter. Prior art Y-adapters typically includes a main body portion that is secured at its distal end to the guide catheter via a luer fitting. The Y-adapter further includes a side branch that defines an infusion port. The main body portion of the Y-adapter is configured to receive a dilatation balloon catheter.

The proximal end of the side branch and the main body portion typically include valves which are known as Tuohy-Borst valves. Tuohy-Borst valves are seals that minimize back-bleeding during the minimally invasive procedure. Each Tuohy-Borst seal includes a gasket having a through lumen and a threadably attached cap. The through lumen is configured to receive a shaft of a dilatation catheter or other minimally invasive device. The cap can be rotatably tightened to compress the gasket and thereby decrease the diameter of the through lumen to form a fluid tight seal about the shaft of the dilatation catheter. However, if the cap of the Tuohy-Borst seal is tightened too much, the dilatation catheter may be damaged or the flow of inflation fluid through the catheter may be restricted so as to make inflation of the balloon of the dilatation catheter difficult. On the other hand, tightening the cap too little may allow back-bleeding through the proximal ends of the side branch and the main body portion of the Y-adapter.

There is a continuing need for improved hemostasis and Y-adapters. Specifically, there is a need for a Y-adapter of efficient design which incorporates a valve member that provides an effective releasable seal about the shaft of a dilatation catheter and provides simplified physician use. The valve member would preferably provide a fluid tight seal about the dilatation catheter to prevent back-bleeding, while minimizing damage to the catheter. In addition, the seal formed by the vale member would not restrict the flow of inflation fluid through the dilatation catheter. It would also be advantageous to provide a valve member which may selectively seal about certain diameter devices while at the same time providing visual feedback as to diameter.

DETAILED DESCRIPTION OF THE INVENTION

The following detailed description should be read with reference to the drawings in which like elements in different drawing are numbered identically. The drawings, which are not necessarily to scale, depict selected embodiments and are not intended to limit the scope of the invention.

Examples of constructions, materials, dimensions, and manufacturing processes are provided for selected elements. All other elements employ that which is known to those skilled in the field of the invention. Those skilled in the art will recognize that many of the examples provided have suitable alternatives that may also be used.

Figure 1:
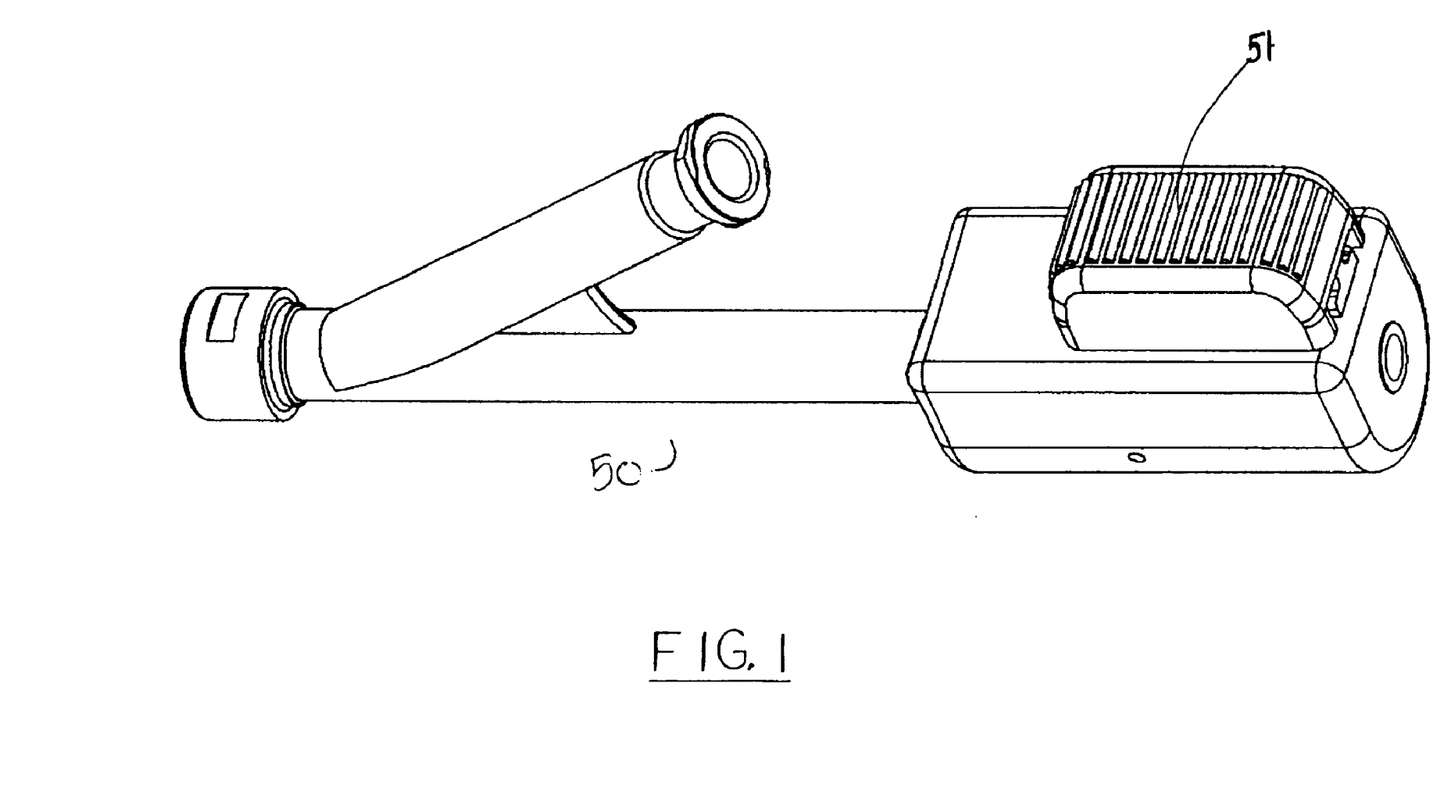
FIG. 1 depicts a y-adapter assembly which incorporates the present invention.

FIG. 1 depicts an embodiment of a y-adapter 50 with actuating button 51. Actuating button 51 may be moved either proximally or distally with the thumb or forefinger and thereby actuate the opening or closing of y-adapter 50.

Figure 2:
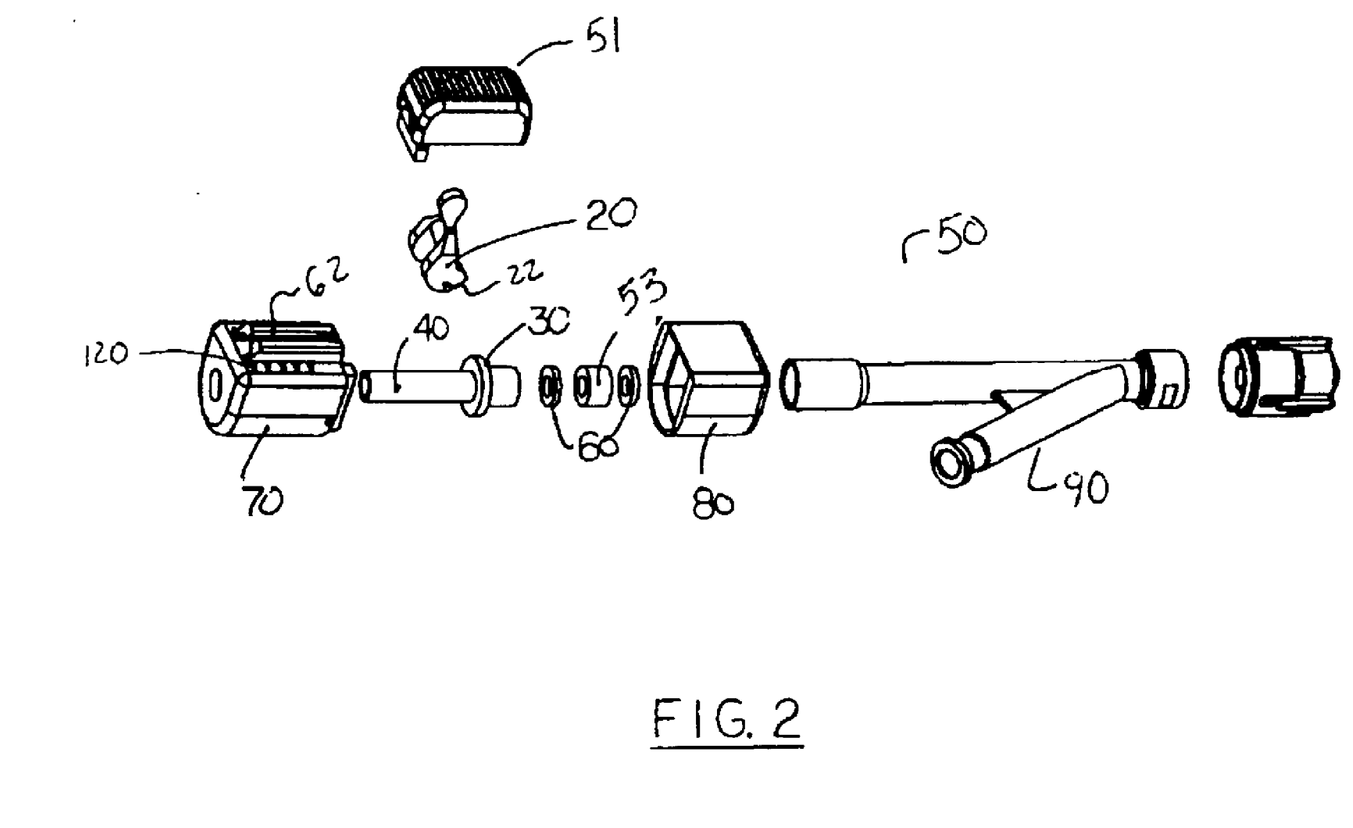
FIG. 2 is an exploded view of the assembly shown in FIG. 1.

FIG. 2 is an exploded view of y-adapter 50. Actuating button 51 is designed to slide within 62 of distal housing 70. Movement of button 51 actuates motion of cam 20. Cam 20 is pinned to proximal housing 80 by pin 22. Accordingly pin 22 defines the axis of rotation of cam 20.

Follower surface 30 is integrally molded with cylinder 40 and serves to compress valve 53 when cylinder 40 is moved axially. Washers 60 may additionally be provided proximally and distally of valve 53. Proximal housing 80 is bonded to body 90 and when brought into contact with distal housing 20, encases cylinder 40, cam 20, valve 53 and washers 60.

Valve 53 may preferably be formed of medical grade silicone such as Wacker R4000. The amount of force needed to compress valve 53 is dependent on the relative hardness of the material used for valve 53. Accordingly, it may be desirable to provide a material for valve 53 that is 20–50 Shore A durometer. Preferably, the durometer of the material of valve 53 may be 30 Shore A. Lower durometer valves or valves with a cutout as shown in FIGS. 7A–D are examples of valves which require less compression to close valve lumen 62. Cylindrical valves with cutouts provide reduced friction and thereby allow physicians to have better tactile feedback during a procedure.

Proximal housing 80, distal housing 70, cylinder 40 and body 90 may be formed of a suitable medical grade polymer. Preferably, proximal housing 80, distal housing 70, cylinder 40 and body 90 may be formed of polycarbonate. Button 51 may be formed of a medical grade acetal-copolymer such as Celcon, natural.

Detents 120 may be formed in proximal housing 70. Detents 120 may be spaced at regular positions along the travel length of button 51 and require button 51 to click into positions which correspond with particular diameters of valve lumen 62. Detents 120 may be conveniently positioned to correspond to atherectomy devices, stent catheters, balloon catheters and guide wire (8 Fr., 5 Fr., 3 Fr. and 0.014 inches respectively). Button 53 may also be moved rapidly such that the valve lumen 62 moves from completely open to completely closed.

In an alternative embodiment, button 51 may be designed such that specified positions along it travel length are indexed by radial teeth (not shown) which project from button 51 and mate with slots in proximal housing 70. In yet another embodiment of button 51, button 51 may have a spring mechanism which may include a coil spring or a leaf spring which maintains the button position but may also be depressed and allow the diameter of valve lumen 62 to be fine tuned.

Figure 3:
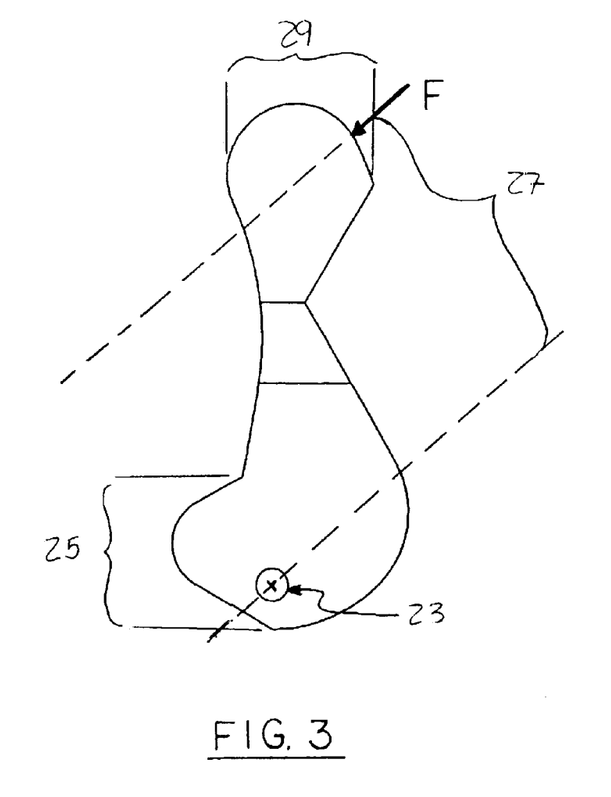
FIG. 3 is an enlarged side view of the cam depicted in FIG. 2.
Figure 4A:
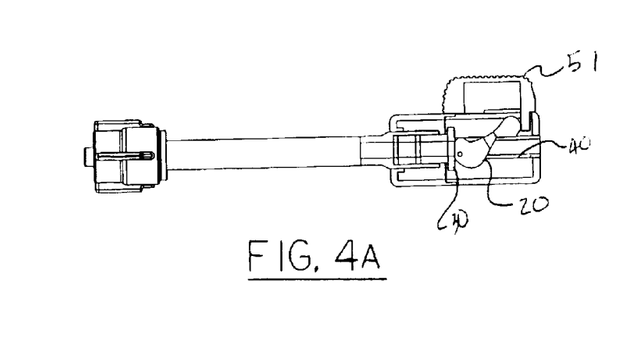
FIG. 4A is a partial side view the assembly of FIG. 1, where the valve is in the fully open position.
Figure 4B:
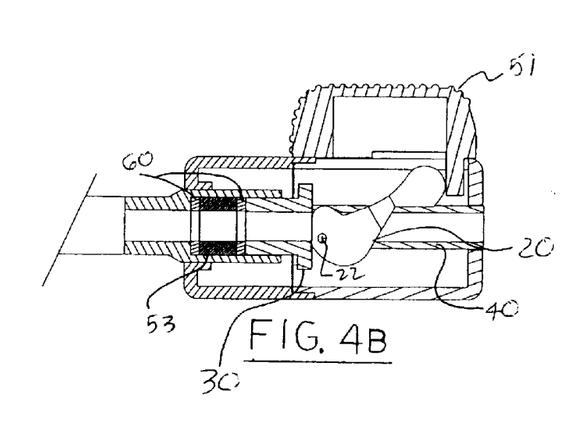
FIG. 4B is an enlarged partial side view the assembly of FIG. 4A.
Figure 4C:
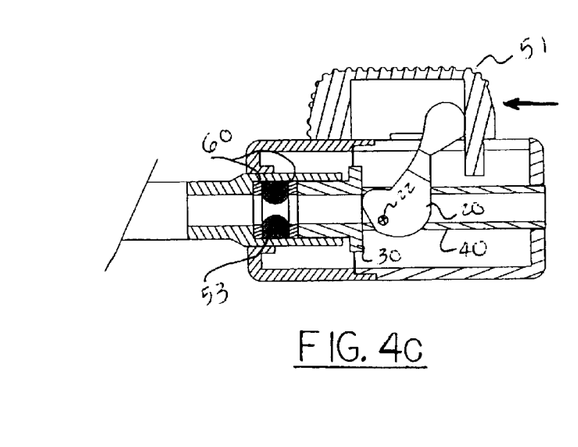
FIG. 4C is a partial side view the assembly of FIG. 4B where the valve is partially closed.
Figure 4D:
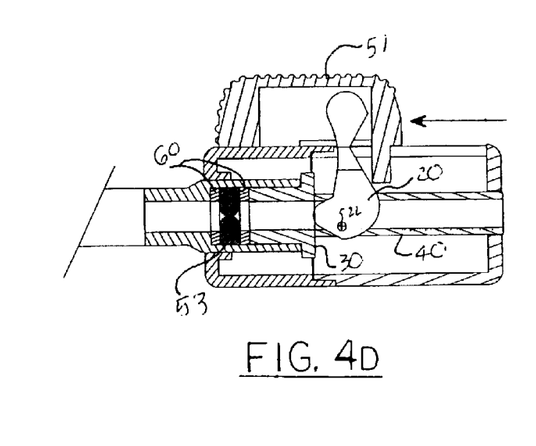
FIG. 4D is a partial side view the assembly of FIG. 4B where the valve is completely closed.

FIG. 3 depicts cam 20 with button contact surface 29 and follower contact surface 25. Mechanical advantage is gained by the moment arm 27 or the perpendicular distance from the point which the button 51 contacts button contact surface 29, with varying force F, to the cam axis 23. Moment arm 27 is a key factor in the amount of force required to actuate button 51 and compress valve 53. The location of cam axis 23 and its position relative to the follower contact surface 25 also is a factor in the mechanical advantage provide by cam 20. The ratio of the distance the button travels axially compared to the axial travel of the follower may be a factor of 3:1 or more depending on the size and design of the cam 20.

To maintain a small profile, the cam 20 should be as small as possible. However, small cam sizes have fairly high stress and therefore require stronger materials of construction. In addition to polycarbonate and other suitable medical grade polymers, filled materials may be required to withstand the high stress. Suitable filled materials may include glass filled ABS or Celcon™.

As may be seen in FIGS. 4A–4D, the linear activation of button 51 rotates cam 20 about pin 22 while the cam contacts the follower surface 30. The follower surface 30 slides the cylinder 40 axially and compresses valve 53 as a function of the contact between follower surface 30 and cam 20. Compression of the valve 53 causes reduction in the lumen diameter of valve 53. Preferably, valve 53 will be sized such that any device may be used. A total range for valve 53 may be 9.6–0 French or 0.125–0 inches.

Figure 5:
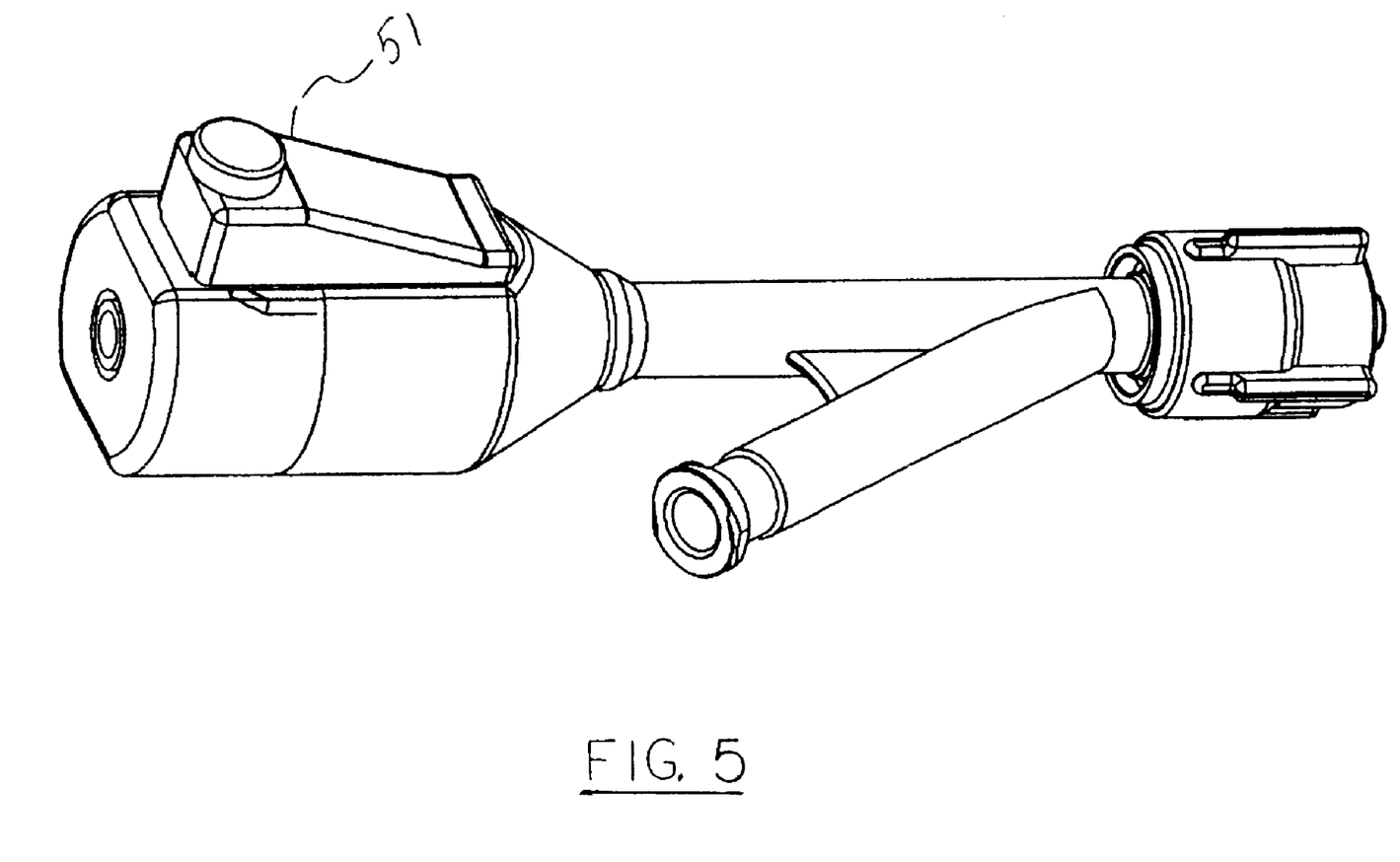
FIG. 5 is a depiction of an alternative y-adapter assembly which incorporates the present invention.
Figure 6:
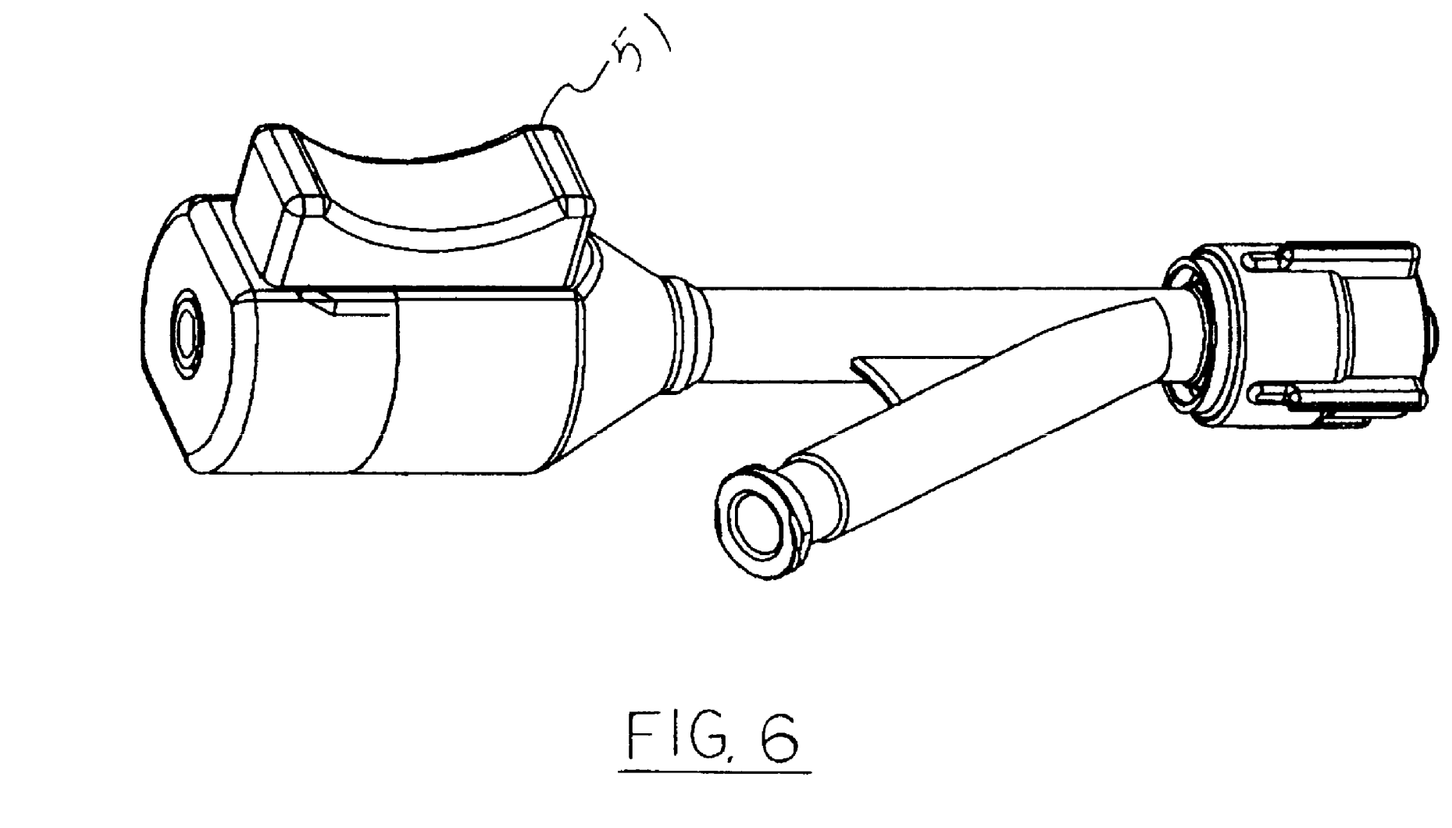
FIG. 6 is a depiction of another alternative y-adapter assembly which incorporates the present invention.
Figure 7A:
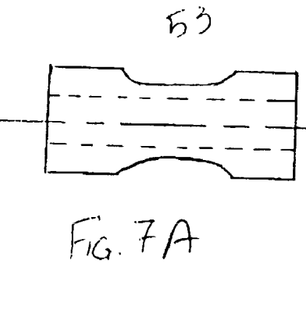
FIG. 7A is a side view of a valve.
Figure 7B:
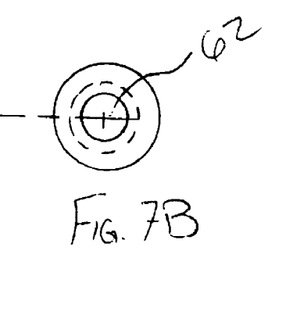
FIG. 7B is an end view of the valve of FIG. 7A.
Figure 7C:
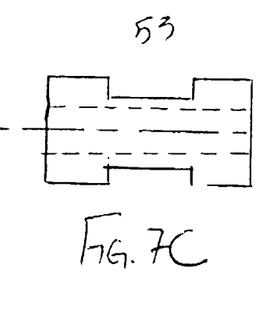
FIG. 7C is a side view of an alternative valve.
Figure 7D:
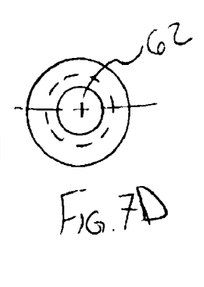
FIG. 7D is an end view of the valve of FIG. 7C.

Ergonomic designs of button 51 may include various shapes or sizes as well as being fully circumferential. These designs allow easy access irrespective of the position of the y-adapter. FIGS. 5 and 6 are examples of alternative button designs 51.

In addition to the embodiments shown, a cylindrical activation surface which encompasses the total circumference of the valve may also be used and will allow for easy access from any angle. Axial adjustment may also include another mechanism which allows the user analog adjustment. Analog adjustment provides for fine tuning of the valve to the required amount of hemostasis and the appropriate feel or lumen size for the particular device within the y-adapter. One such method of achieving analog adjustment is through the addition of a cylindrical threaded surface which can be adjusted for fine tuning.

Figure 8:
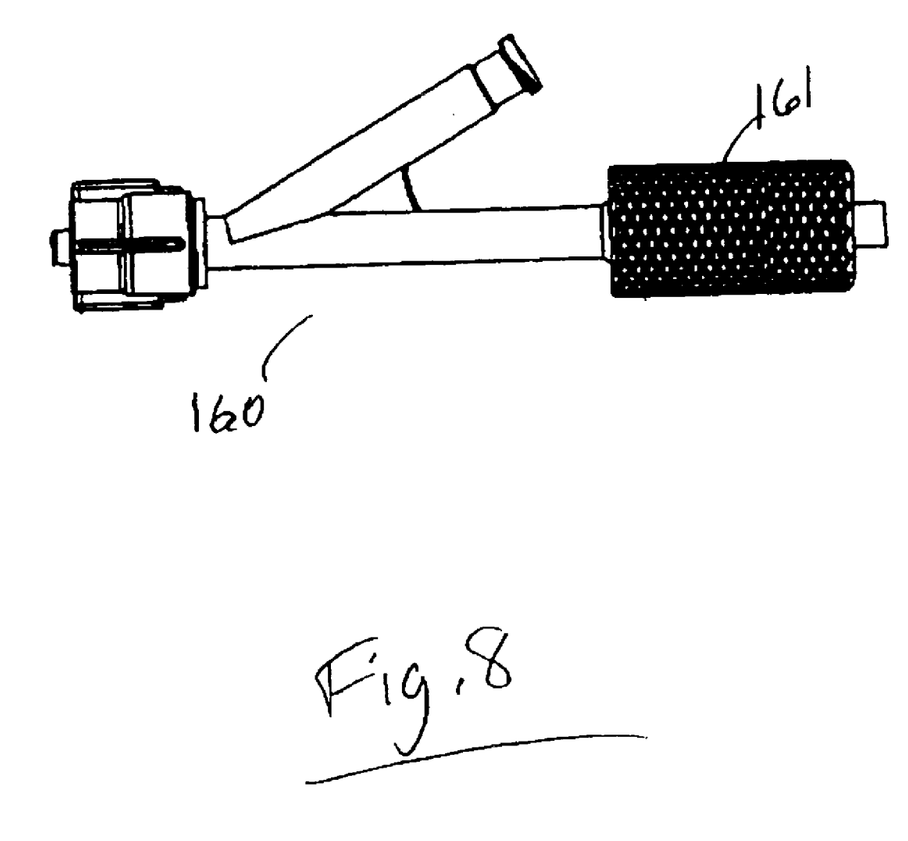
FIG. 8 depicts an axially activated Y-adapter assembly.
Figure 9:
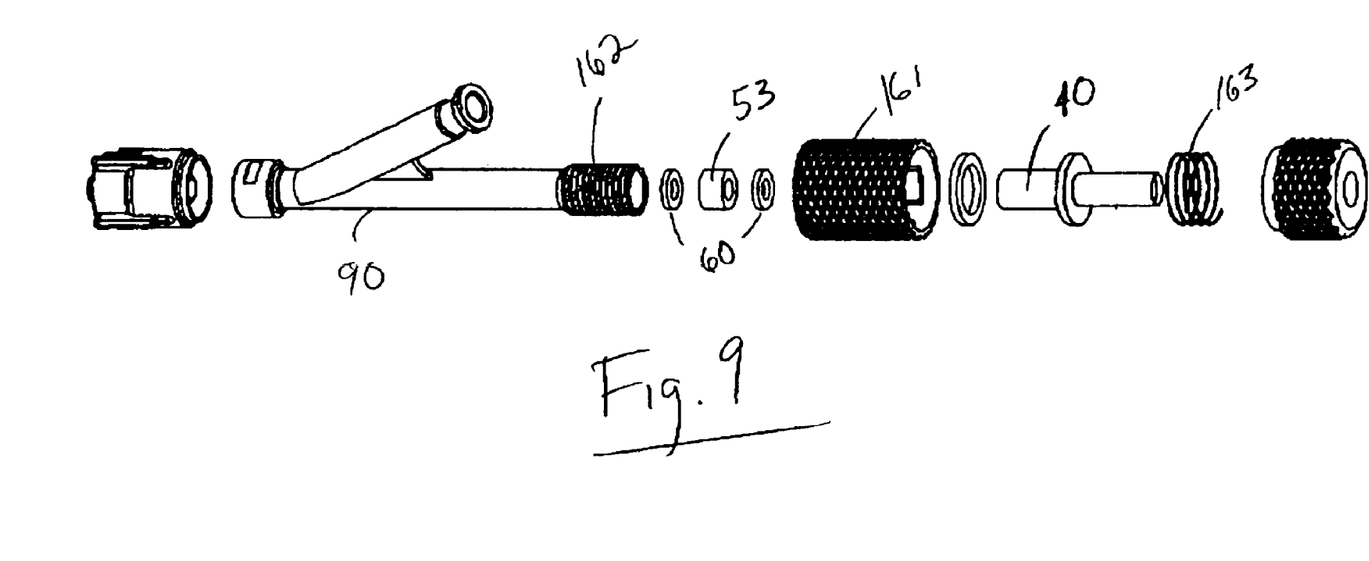
FIG. 9 is an exploded view of the assembly shown in FIG. 8.
Figure 10:
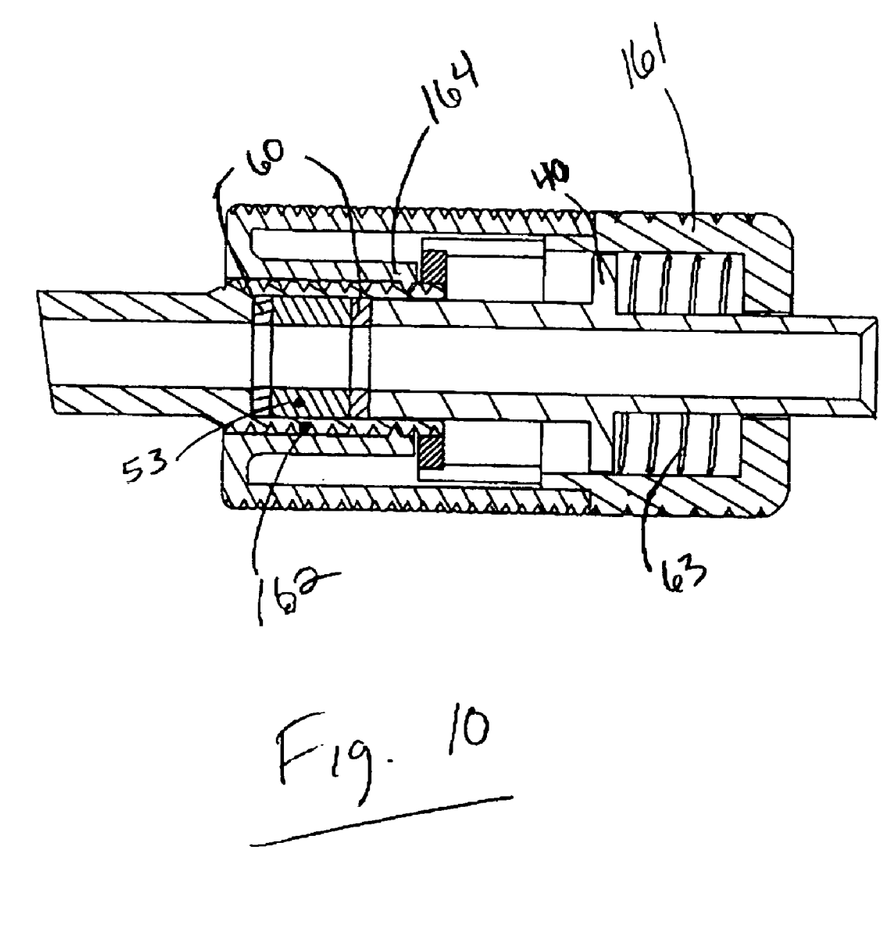
FIG. 10 is a partial sectioned side view of FIG. 8.

Mechanisms other than a cam design may also be employed to achieve the main objective of the invention. One such mechanism would provide pure axial translation to compress the valve 53. FIG. 8 depicts this embodiment of a y-adapter 160 with a cylindrical actuating button, hereafter called a collar 161. The cylindrical actuating collar 161 may be moved either proximally or distally with the thumb or forefingers and thereby actuate the opening or closing of the y-adapter. FIG. 9 is an exploded view of the assembly shown in FIG. 8. Various lumen sizes would be achieved by axially sliding the collar 161 along the adjusting threads 162 to snap fit into certain positions. The partial sectioned side view in FIG. 10 shows how the snap fit would be achieved by axially located spring arms 164 located within the adjusting threads 162. The spring arms deflect when forced to move axially and snap into the thread minor diameter in either direction to achieve closing or opening of the y-adapter lumen. Alternately, the collar 161 may be rotated to achieve fine tuning of the y-adapter lumen. A spring mechanism 163 would increase the ratio of manual motion to valve compression, thereby providing the physician with greater tactile feedback. The spring 163 actuates the cylindrical push rod 40 similar to that found in the embodiment of FIG. 2. The pushrod 40 then compresses valve 53 to reduce the lumen size. A secondary mechanism may be adjusted for fine tuning at each interval.

While the specification describes the preferred designs, materials, methods of manufacture and methods of use, those skilled in the art will appreciate the scope and spirit of the invention with reference to the appended claims.

We claim:

1. A variable diameter hemostasis system comprising:
   a body having a bore therethrough;
   a hemostasis valve mounted in the bore:
   an actuator moveably attached to the body and configured to compress the hemostasis valve; and
   a cam positioned on the body and configured to releasably restrain the actuator from moving and configured to exert a force to thereby selectively compress the hemostasis valve.

2. The hemostasis valve of claim 1 comprising a cylinder having a bore therethrough.

3. The hemostasis valve of claim 1 comprising cutouts to selectively change the compressive response of the hemostasis valve.

4. The hemostasis valve of claim 1 formed of a medical grade polymer.

5. The actuator of claim 1 further comprising:
a button slideably attached to an exterior of the body;
a lever slideably coupled to the button, the lever having a pivot point, a lever arm and a cam surface;
a pin rotateably fixed to the body and rotateably fixed to the pivot point of the lever arm; and
a cylinder slideably positioned within the bore of the body, the cylinder having a follower surface suitable for contact with the cam and a distal surface suitable for compressing the hemostasis valve.

6. The button of claim 5 configured to be held in place by detents in the body and thereby provide indexing closure of the hemostasis valve.

7. The detents of claim 6 spaced along a longitudinal axis of the body such that the detents correspond to standard sizes of atherectomy devices, stent delivery catheters, balloon catheters or guide wires.

8. The actuator of claim 1 comprising:
a collar mounted about the body, the collar having at least one springarm with an engaging member mounted on the at least one springarm; and
female threads surrounding the body and configured to mate with the engaging member of the at least one spring arm, the at least one springarm being moveable when the collar is axially moved.

9. The actuator of claim 8 further comprising a spring mounted about the body such that axial movement of the collar is enhanced.

10. A Y adapter comprising:
a Y shaped body having a main section with a first lumen therethrough and a branch section with second lumen therethrough, the first lumen in fluid connection with the second lumen;
a hemostasis valve mounted within the first lumen;
a rotateable link having a cam surface and a lever arm, the link pivoting about a pivot point and aligned such that force transmitted to the lever arm will be magnified and cause the cam surface to exert a force to compress the hemostasis valve; and
an axially moveable actuator, configured to transmit axially applied force to the lever arm of the rotateable link.

11. The Y adapter of claim 10 further comprising a cylinder having a follower surface suitable for contact with the cam surface and a face suitable for contacting the hemostasis valve, the cylinder located within the first lumen between the hemostasis valve and the rotateable link and configured to convert rotational force from the rotateable link to compressive force on the hemostasis valve.

12. The hemostasis valve of claim 10 comprising a cylindrical medical grade polymer, wherein force applied along an axis of the cylinder will cause the cylinder to constrict a lumen through the cylinder.

13. The axially moveable actuator of claim 12 comprising detent means configured to correspond to particular constricted diameters of the hemostasis valve.

14. A system for selectively narrowing a lumen of a vascular access device comprising:
a hemostasis valve positioned within the vascular access devices; and
a means for selectively narrowing the hemostasis valve, the means for selectively narrowing having a cam providing discrete amounts of force to the hemostasis valve.

15. The system for selectively compressing the hemostasis of claim 14 wherein the discrete amounts pressure correspond to standard sizes of atherectomy devices, stent delivery catheters, balloon catheters or guide wires.

16. The system of claim 15 further comprising visual markers configured to correspond to incremental diameters of the hemostasis valve.

* * * * *